US006187034B1

United States Patent
Frantzen

(10) Patent No.: US 6,187,034 B1
(45) Date of Patent: Feb. 13, 2001

(54) SEGMENTED STENT FOR FLEXIBLE STENT DELIVERY SYSTEM

(76) Inventor: John J. Frantzen, 424 Poker Flat Rd., Copperopolis, CA (US) 95228

(*) Notice: Under 35 U.S.C. 154(b), the term of this patent shall be extended for 0 days.

(21) Appl. No.: 09/229,856

(22) Filed: Jan. 13, 1999

(51) Int. Cl.[7] .................................................. A61F 2/06
(52) U.S. Cl. .......................................... 623/1.11; 623/1.15
(58) Field of Search .................................. 623/1.11, 1.15, 623/1.16, 1.21; 604/96

(56) References Cited

U.S. PATENT DOCUMENTS

| D. 380,266 | 6/1997 | Boatman et al. . |
| D. 380,831 | 7/1997 | Kavteladze et al. . |
| 4,704,126 | 11/1987 | Baswell et al. . |
| 4,856,516 | * 8/1989 | Hillstead .............................. 623/1.15 |
| 4,858,264 | 8/1989 | Reinhart . |
| 4,936,057 | 6/1990 | Rhoades . |
| 5,104,404 | 4/1992 | Wolff . |
| 5,108,417 | 4/1992 | Sawyer . |
| 5,133,732 | 7/1992 | Wiktor . |
| 5,139,480 | 8/1992 | Hickle et al. . |
| 5,195,984 | 3/1993 | Schatz . |
| 5,199,226 | 4/1993 | Rose . |
| 5,242,399 | 9/1993 | Lau et al. . |
| 5,314,444 | 5/1994 | Gianturco . |
| 5,383,892 | 1/1995 | Cardon et al. . |
| 5,421,955 | 6/1995 | Lau et al. . |
| 5,423,849 | 6/1995 | Engelson et al. . |
| 5,425,739 | 6/1995 | Jessen . |
| 5,441,515 | 8/1995 | Khosravi et al. . |
| 5,443,477 | 8/1995 | Marin et al. . |
| 5,443,496 | 8/1995 | Schwartz et al. . |
| 5,449,373 | 9/1995 | Pinchasik et al. . |
| 5,485,667 | 1/1996 | Kleshinski . |
| 5,494,029 | 2/1996 | Lane et al. . |
| 5,496,277 | 3/1996 | Termin et al. . |
| 5,507,767 | 4/1996 | Maeda et al. . |
| 5,507,771 | 4/1996 | Gianturco . |

(List continued on next page.)

FOREIGN PATENT DOCUMENTS 95302708    4/1995   (EP) .

OTHER PUBLICATIONS

Patrick W. Serruys and Michael JB Kutryk, Handbook of Coronary Stents, 1998, pp. 45, 55, 78, 103, 112, 132, 158, 174, 185, 190, 207, 215, 230, 239, Second Edition, Martin Dunitz, United Kingdom.

* cited by examiner

Primary Examiner—David H. Willse
Assistant Examiner—Suzette J. Jackson
(74) Attorney, Agent, or Firm—Heisler & Associates

(57) ABSTRACT

A segmented stent 10 is disclosed as part of a flexible stent delivery system. The segmented stent 10 includes multiple segments 80 axially spaced from each other with unspanned gaps 45 between the segments 80. When the segmented stent 10 is flexed in a manner causing a central axis A to bend, the segments 80 maintain their form without significant flexing and the unspanned gaps 45 between the segments 80 are altered to provide flexing between the segments 80. A flexible balloon 110 is beneficially provided for delivery of the segmented stent 10 which includes separate cylindrical sections 120 which have an axial length which matches the axial length of each segment 80. Notches 130 are located between the cylindrical sections 120 in the flexible balloon 110 so that areas of flexing in the flexible balloon 110 line up with the unspanned gaps 45 in the segmented stent 10. Because the segments 80 are not attached together, the segmented stent 10 can be configured with a variety of different numbers and types of segments 80 having different sizes and different other properties in a custom manner as desired by the surgeon for maximum therapeutic effect of the segmented stent 10 once implanted into a body lumen L.

15 Claims, 6 Drawing Sheets

U.S. PATENT DOCUMENTS

| | | |
|---|---|---|
| 5,514,154 | 5/1996 | Lau et al. . |
| 5,522,882 | 6/1996 | Gaterud et al. . |
| 5,531,741 | 7/1996 | Barbacci . |
| 5,545,210 | 8/1996 | Hess et al. . |
| 5,549,662 | 8/1996 | Fordenbacher . |
| 5,549,663 | 8/1996 | Cottone . |
| 5,554,181 | 9/1996 | Das . |
| 5,562,641 | 10/1996 | Flomenblit et al. . |
| 5,562,728 | 10/1996 | Lazarus et al. . |
| 5,569,295 | 10/1996 | Lam . |
| 5,578,149 | 11/1996 | DeScheerder et al. . |
| 5,591,195 | 1/1997 | Taheri et al. . |
| 5,591,197 | 1/1997 | Orth et al. . |
| 5,591,223 | 1/1997 | Lock et al. . |
| 5,591,226 | 1/1997 | Trerotola et al. . |
| 5,591,230 | 1/1997 | Horn et al. . |
| 5,603,721 | 2/1997 | Lau et al. . |
| 5,605,530 | 2/1997 | Fischell et al. . |
| 5,607,442 | 3/1997 | Fischell et al. . |
| 5,607,445 | 3/1997 | Summers . |
| 5,618,299 | 4/1997 | Khosravi et al. . |
| 5,624,411 | 4/1997 | Tuch . |
| 5,630,840 | 5/1997 | Mayer . |
| 5,632,760 | 5/1997 | Sheiban et al. . |
| 5,632,763 | 5/1997 | Glastra . |
| 5,632,771 * | 5/1997 | Boatman et al. .................. 623/1.16 |
| 5,634,941 | 6/1997 | Winston et al. . |
| 5,636,641 | 6/1997 | Fariabi . |
| 5,637,113 | 6/1997 | Tartaglia et al. . |
| 5,697,971 | 12/1997 | Fischell et al. . |
| 5,718,713 | 2/1998 | Frantzen . |
| 5,741,327 | 4/1998 | Frantzen . |
| 5,746,691 | 5/1998 | Frantzen . |
| 5,843,175 | 12/1998 | Frantzen . |
| 5,868,782 * | 2/1999 | Frantzen ............... 623/1.15 |
| 5,879,381 * | 3/1999 | Moriuchi et al. ............... 623/1.16 |
| 5,902,332 * | 5/1999 | Schatz ............... 623/1.16 |
| 6,033,434 * | 3/2000 | Borghi ............... 623/1.15 |

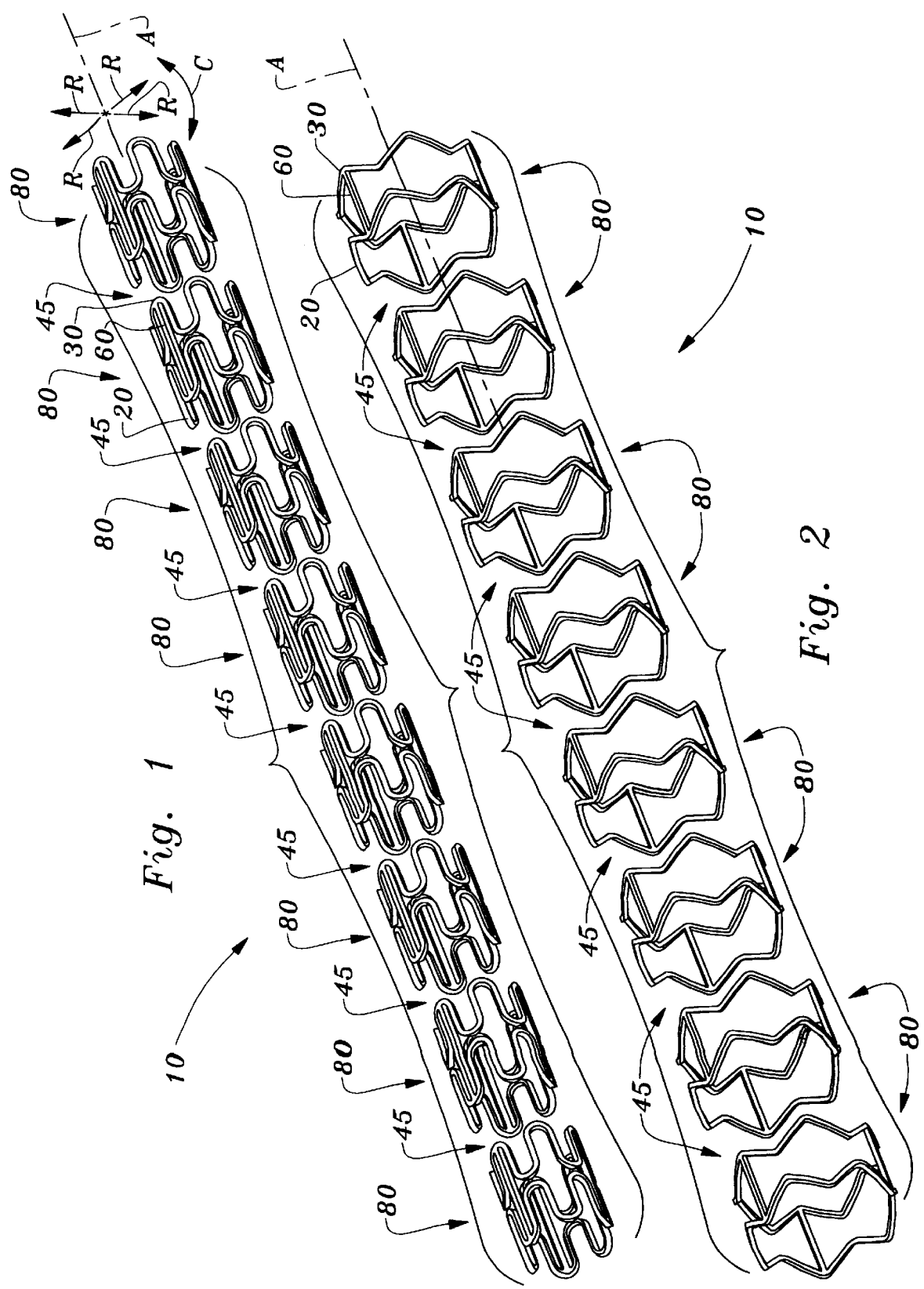

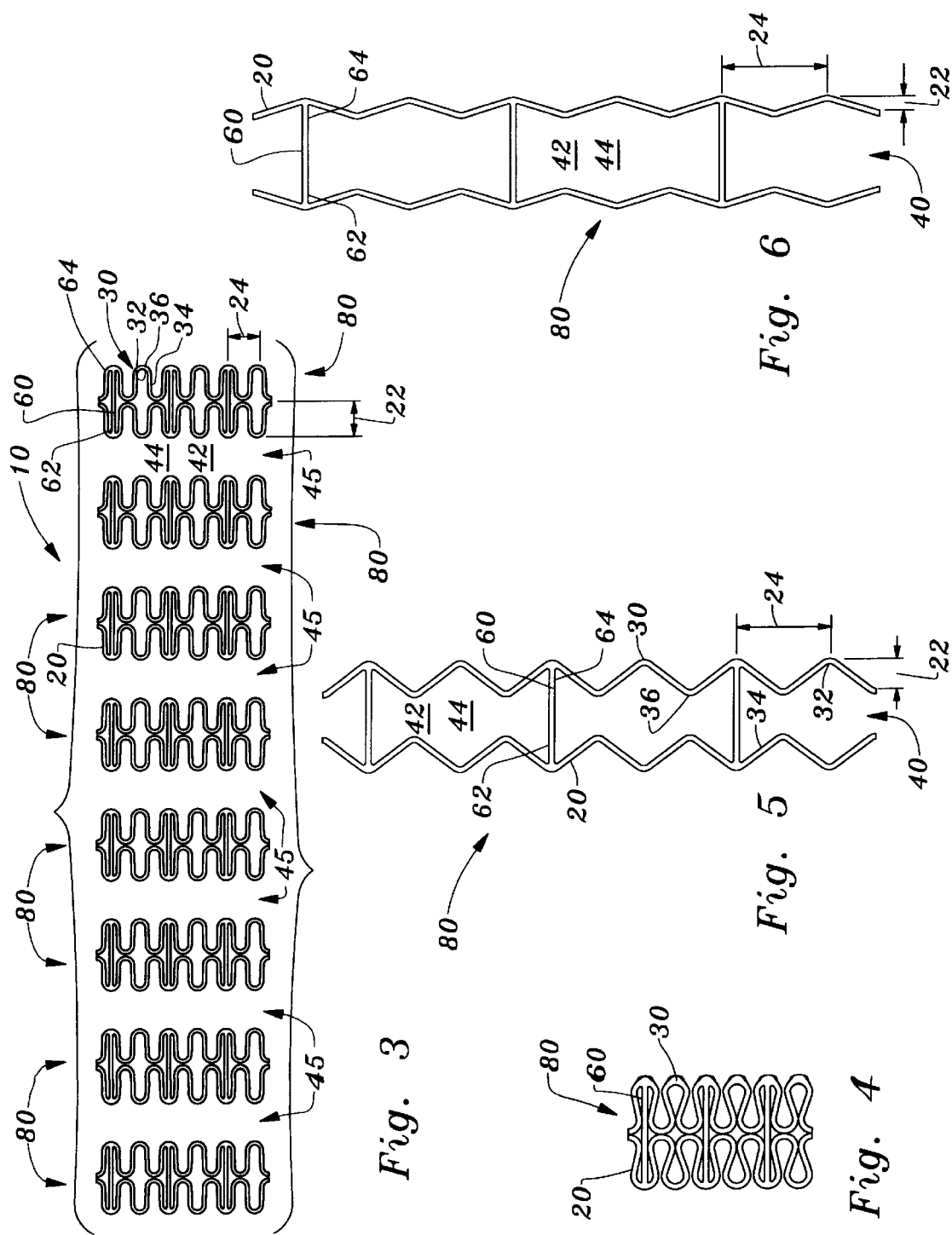

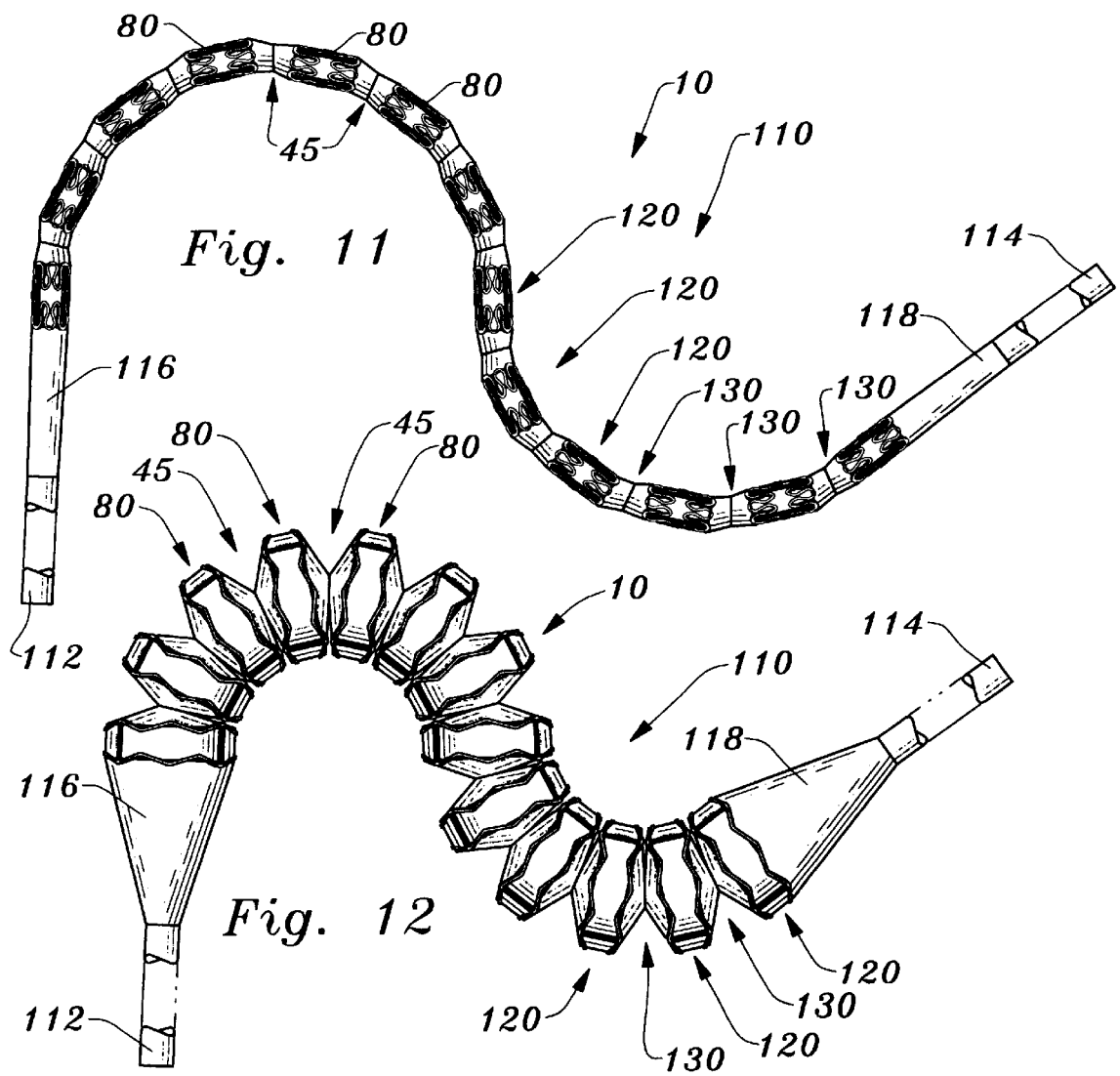
Fig. 11
Fig. 12
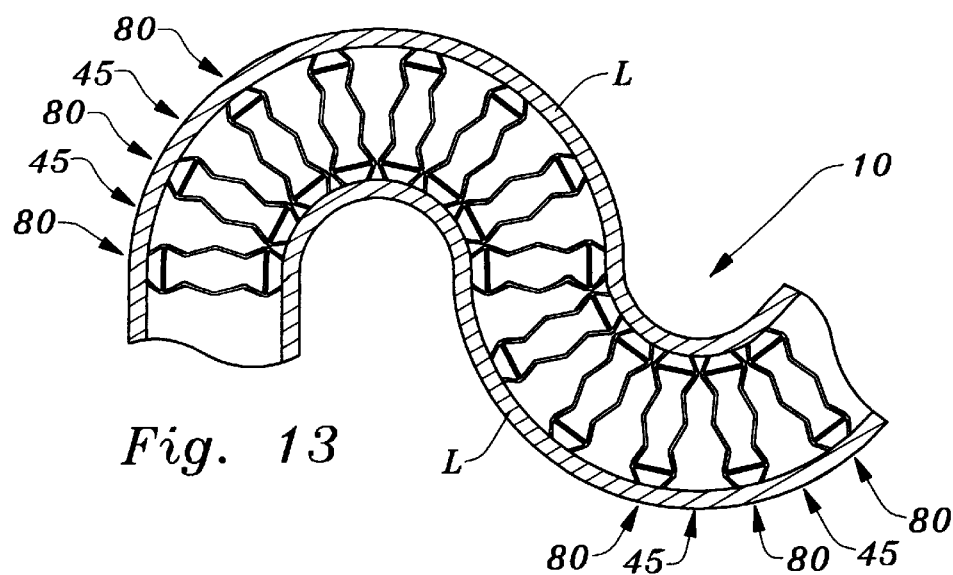
Fig. 13

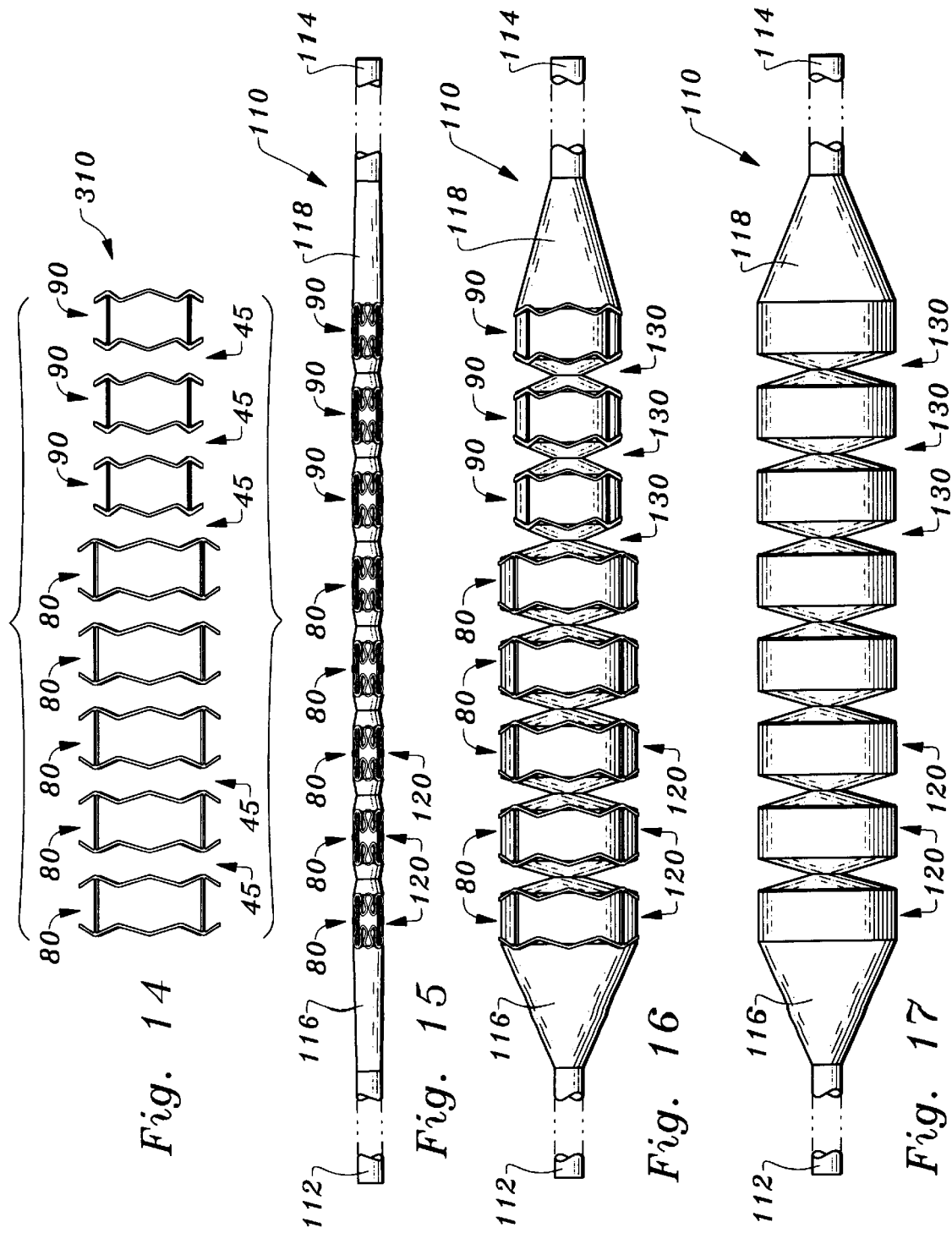

SEGMENTED STENT FOR FLEXIBLE STENT DELIVERY SYSTEM

FIELD OF THE INVENTION

The following invention relates to surgical stents for implantation into a body lumen such as an artery to support the lumen. More particularly, this invention relates to surgical stents which are highly flexible and can be readily adjusted and customized to match particular contour characteristics of the body lumen and the particular treatment needs for the body lumen at the implantation site.

BACKGROUND OF THE INVENTION

Surgical stents have long been known which can be surgically implanted into a body lumen, such as an artery, to reinforce, support, repair or otherwise enhance the performance of the lumen. For instance, in cardiovascular surgery it is often desirable to place a stent in the coronary artery at a location where the artery is damaged or is susceptible to collapse. The stent, once in place, reinforces that portion of the artery allowing normal blood flow to occur through the artery. One form of stent which is particularly desirable for implantation in arteries and other body lumens is a cylindrical stent which can be radially expanded from a first smaller diameter to a second larger diameter. Such radially expandable stents can be inserted into the artery by being located on a catheter and fed internally through the arterial pathways of the patient until the unexpanded stent is located where desired. The catheter is fitted with a balloon or other expansion mechanism which exerts a radial pressure outward on the stent causing the stent to expand radially to a larger diameter. Such expandable stents exhibit sufficient rigidity after being expanded that they will remain expanded after the balloon has been removed.

Radially expandable stents come in a variety of different configurations to provide optimal performance in various different particular circumstances. For instance, the patents to Lau (U.S. Pat. Nos. 5,514,154, 5,421,955, and 5,242,399), Baracci (U.S. Pat. No. 5,531,741), Frantzen (U.S. Pat. Nos. 5,718,713, 5,741,327, 5,746,691), Gaterud (U.S. Pat. No. 5,522,882), Gianturco (U.S. Pat. Nos. 5,507,771 and 5,314,444), Termin (U.S. Pat. No. 5,496,277), Lane (U.S. Pat. No. 5,494,029), Maeda (U.S. Pat. No. 5,507,767), Marin (U.S. Pat. No. 5,443,477), Khosravi (U.S. Pat. No. 5,441,515), Jessen (U.S. Pat. No. 5,425,739), Hickle (U.S. Pat. No. 5,139,480), Schatz (U.S. Pat. No. 5,195,984), Fordenbacher (U.S. Pat. No. 5,549,662), and Wiktor (U.S. Pat. No. 5,133,732), each include some form of radially expandable stent for implantation into a body lumen. Other prior art stents are compiled in the Handbook of Coronary Stents, Second Edition, produced by the Rotterdam Thoraxcenter Interventional Cardiology Group.

Most of these prior art stents suffer from undesirable axial contraction when radially expanded. Stents can be made to resist axial contraction upon radial expansion by including axial elements therein extending continuously from a first end of the stent to a second end of the stent. However, such continuous axial elements tend to make the stent stiff and exhibit less flexibility characteristics than needed to allow the stent to be easily passed through tortuous arterial pathways or other tightly curving body lumens effectively. Some of these prior art stents, such as the stents described in the patents to Frantzen resist axial contraction upon radial expansion by locating axial elements offset from each other and within troughs of adjacent circumferential elements. While flexibility does improve somewhat by offsetting such axial elements, additional flexibility is often needed.

In addition to flexibility drawbacks, known prior art stents typically are provided with a pre-configured contour having various different pre-radial expansion and post radial expansion diameters. These prior art stents have other non-variable predetermined characteristics such as strength characteristics, radiopacity characteristics, biocompatibility characteristics, flexibility characteristics and axial length characteristics. Body lumens in which stent implantation is indicated can vary in a variety of different ways. Hence, pre-configured stents are not always provided with a contour and other characteristics which optimally match the needs of the body lumen where implantation is desired. Accordingly, a need exists for a stent which can be custom configured by the surgeon or custom ordered by the surgeon for ready assembly by a qualified technician to the surgeon's specifications to provide the treatment desired within the body lumen where implantation of the stent is to occur.

Also, stent flexibility of known prior art stents is not well matched with flexibility of stent delivery and expansion balloons. Rather, known stent delivery and expansion balloons typically are provided with a cylindrical contour which can be inflated and radially expanded to just a few different radial sizes. Accordingly, a need exists for a balloon which can be configured to have flexibility and radial expansion characteristics which more closely match the flexibility and radial expansion characteristics of stents with which the balloon is mated.

SUMMARY OF THE INVENTION

The segmented stent of this invention includes a series of circumferential elements axially spaced from each other along a central axis of the stent. Each circumferential element is configured so that it can be expanded radially from a first collapsed diameter to a second expanded diameter. This expanded diameter can either be a diameter of maximum radial expansion where the circumferential element is expanded nearly to the point where it is circular in form or can be limited to an intermediate amount where the circumferential elements still include an undulating form as the circumferential elements circumscribe the central axis.

Gaps are located between adjacent circumferential elements which space the circumferential elements axially away from each other. Some of the gaps are spanned gaps that include axial elements joining a pair of circumferential elements adjacent the spanned gaps. Other gaps are unspanned gaps with no axial elements provided between the pair of circumferential elements adjacent the unspanned gaps. Hence, the stent is segmented into separate segments with unspanned gaps located between each of the segments and spacing the segments axially away from each other. The unspanned gaps in the segmented stent provide areas where the stent can be flexed to cause the central axis of the stent to bend without resistance. The segments maintain their form both before and after radial expansion without any appreciable flexing or axial length adjustment.

Because the individual segments of the stent are not actually connected together, the stent can be made up of a customizable different number of segments to increase or decrease an overall axial length of the stent. Also, segments of differing maximum diameters of radial expansion, differing radiopacity, differing strength or other differing characteristics can be matched together as segments in a common segmented stent which will have the contour and performance characteristics desired by the surgeon for implantation into the body lumen.

The segmented stent is preferably part of a flexible stent delivery system which additionally includes a flexible balloon particularly configured to support the segments of the stent before and during radial expansion of the stent. The balloon includes cylindrical sections spaced axially from each other by notches. The notches define regions on the balloon where flexing of the balloon is more readily facilitated than at the cylindrical sections. The segments of the segmented stent are oriented so that one segment is adjacent each cylindrical section and so that the unspanned gaps are aligned with the notches. Hence, regions on the stent where flexibility is provided are aligned with regions on the flexible balloon where flexibility is provided.

OBJECTS OF THE INVENTION

Accordingly, a primary object of the present invention is to provide a stent of high flexibility which includes separate segments spaced axially from adjacent segments by unspanned gaps.

Another object of the present invention is to provide a surgical stent which exhibits a high degree of axial flexibility to allow a central axis of the stent to bend along with tightly curving body lumens.

Another object of the present invention is to provide a stent which includes separate segments axially spaced from each other by unspanned gaps with the separate segments having differing dimensional or other characteristics to match the characteristics desired by the surgeon for the stent.

Another object of the present invention is to provide a stent delivery system including a segmented stent and a flexible balloon with flexible regions on the balloon aligned with regions of flexibility on the stent.

Another object of the present invention is to provide a surgical stent which can be either radially expanded to a diameter of maximum radial expansion or only partially radially expanded from an initial collapsed configuration.

Another object of the present invention is to provide a surgical stent which can be custom sized axially to have a length corresponding to a desired length for the region within the body lumen to be supported by the stent.

Another object of the present invention is to provide a surgical stent which can be readily configured to have varying diameters of maximum radial expansion at different points along an axial length of the stent to match the needs of the body lumen at the implantation site.

Other further objects of the present invention will become apparent from a careful reading of the included drawing figures, the claims and detailed description of the invention.

BRIEF DESCRIPTION OF THE DRAWINGS

FIG. 1 is a perspective view of the segmented stent of this invention as it appears when initially formed and before collapsing radially onto a balloon for implantation into a body lumen.

FIG. 2 is a perspective view of that which is shown in FIG. 1 after radial expansion of the segmented stent of this invention.

FIG. 3 is a cylindrical projection of that which is shown in FIG. 1 revealing the specific details in the arrangement of circumferential elements and axial elements within the segmented stent of this invention.

FIG. 4 is a cylindrical projection of a single segment of the segmented stent after the segment is collapsed to a minimum diameter which is exhibited by the stent segment during implantation and before any radial expansion of the segment.

FIG. 5 is a cylindrical projection of that which is shown in FIG. 4 after partial radial expansion of the segment.

FIG. 6 is a cylindrical projection of that which is shown in FIG. 4 after the segment has been radially expanded to a diameter of maximum radial expansion.

FIG. 11 is a front elevation view of a variation on the segmented stent and flexible balloon shown in FIG. 7 with thirteen segments collapsed onto a flexible balloon which has not yet been inflated and radially expanded. The balloon includes thirteen cylindrical sections. The segmented stent and flexible balloon are flexed to illustrate typical flexing of the flexible balloon and segmented stent during implantation into a body lumen.

FIG. 12 is a front elevation view of that which is shown in FIG. 11 after radial expansion of the flexible balloon and segmented stent.

FIG. 13 is a front elevation view of that which is shown in FIG. 12 after the flexible balloon has been deflated and removed and showing the body lumen adjacent to the expanded segmented stent.

FIG. 14 is a front elevation view of a segmented stent featuring varying diameter segments and with portions of the stent on a rear side of the stent occluded to enhance clarity of the portions of the stent segments shown.

FIG. 15 is a front elevation view of that which is shown in FIG. 14 before radial expansion of the segmented stent and with the segmented stent collapsed down onto an uninflated flexible balloon.

FIG. 16 is a front elevation view of that which is shown in FIG. 15 after inflation and radial expansion of the flexible balloon and radial expansion of the segmented stent with varying diameter segments.

FIG. 17 is a front elevation view of the flexible balloon as it would appear if it were inflated without the constricting effect of the small segments of the stent of FIG. 16.

DESCRIPTION OF THE PREFERRED EMBODIMENT

Figure 7:
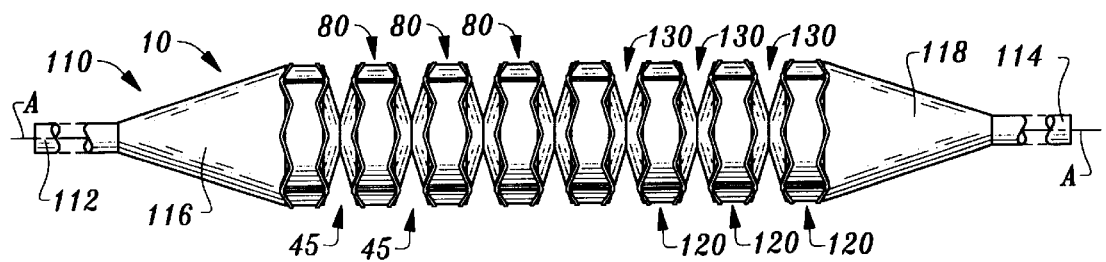
FIG. 7 is a front elevation view of that which is shown in FIG. 2, with the segmented stent located upon a flexible balloon after being radially expanded.

Referring to the drawings, wherein like reference numerals represent like parts throughout the various drawing figures, reference numeral 10 is directed to a segmented stent (FIGS. 1 and 2) for surgical implantation and radial expansion (along arrow R) within a body lumen to support the body lumen. The segmented stent 10 includes multiple separate segments 80 which are axially spaced from each other (along the central axis A) by unspanned gaps 45 so that the segments 80 can readily flex relative to each other.

In essence, and with particular reference to FIGS. 1–6, the primary features of the segmented stent 10 are described.

The stent 10 includes a series of circumferential elements 20 circumscribing a central axis A (FIGS. 1 and 2) of the stent 10 and located in separate planes spaced axially from each other by gaps 40, 45 (FIGS. 3 and 5). Each circumferential element 20 is configured with a wave-like series of bends 30 therein (FIG. 1). Each bend 30 defines either a trough 32 or a crest 36 (FIG. 3) depending on the direction from which the bend 30 is viewed. The trough 32 defines a portion of each bend 30 which is most distant from adjacent circumferential elements 20 that the trough 32 faces. The crest 36 defines a portion of each bend 30 which is closest to adjacent circumferential elements 20 which the crest 36 faces.

Each gap 40 (FIG. 5) is spanned by at least one axial element. The axial elements are preferably tie bars 60. The tie bars 60 preferably extend linearly between troughs 32 on opposite sides of the gap 40 spanned by the tie bar 60. Each gap 45 is unspanned, dividing the stent 10 into separate segments 80 spaced axially from each other. The unspanned gaps 45 provide flexibility to the stent 10 and allow the stent 10 to be easily custom designed to include various numbers of segments 80 having different size and other characteristics.

More specifically, and with particular reference to FIGS. 1–6, the details of the configuration of the preferred embodiment of the surgical stent 10 are described. The contour of the stent 10 is generally outlined by the series of circumferential elements 20 circumscribing the central axis A (FIGS. 1 and 2) of the stent 10. Each circumferential element 20 includes a wave-like series of bends 30. Portions of each bend 30 which are most distant from adjacent circumferential elements 20 define troughs 32 (FIG. 3). Portions of each bend 30 which are closest to adjacent circumferential elements 20 define crests 36. A midway point between each trough 32 and crest 36, where a curvature of the bend 30 changes, defines an inflection point 34. Specifically, each trough 32 actually defines a region between adjacent inflection points 34 which is most distant from the adjacent circumferential element 20 and the crest 36 defines a region between adjacent inflection points 34 which are closest to the adjacent circumferential element 20.

Whether a portion of the bend 30 is a trough 32 or a crest 36 is a matter of perspective depending on what side of the bend 30 is being viewed. One side of a bend 30 defines a crest 36 closest to an adjacent circumferential element 20 and the other side of the bend 30 defines a trough 32 most distant from an adjacent circumferential element 20.

The dimensions of the bends 30 forming each circumferential element 20 can be quantified with reference to an amplitude 22 (FIGS. 3, 5 and 6) and a wave length 24. The actual measurements for the amplitudes 22 and wave lengths 24 for the stent 10 can vary depending on the particular application for which the surgical stent 10 is configured. Also, the amplitudes can vary between circumferential elements 20 so that the stent 10 can taper in a non-cylindrical fashion between a first end 12 and a second end 14 of the stent 10. As the stent 10 is radially expanded, along arrow R (FIG. 1) the amplitude 22 will decrease in size and the wave length 24 will increase. The increase in wave length 24 will increase a circumferential size of the stent 10 (arrow C of FIG. 3), allowing the stent 10 to expand radially and yet still maintain the circumferential elements 20 in a configuration completely circumscribing the central axis A (FIGS. 1 and 2) of the stent 10.

Because the amplitude 22 decreases when the stent 10 is radially expanded, the stent 10 has a natural tendency to contract axially, along arrow A, when the stent 10 is radially expanded. However, because this stent 10 has circumferential elements 20 joined together with axial elements which connect at troughs 32 in the circumferential elements 20, this axial contracting tendency is nullified by this stent 10.

The stent 10 is preferably made from stainless steel or other bio-compatible materials. The stent 10 is configured so that structures forming the stent 10, including the elements 20 can bend somewhat without breaking, to facilitate radial expansion of the stent 10. Alternatively, the stent 10 can be made from nickel titanium alloys which are both biocompatible and have an ability to change shape and radially expand when transforming between austenite and martensite solid phases.

Figure 8:
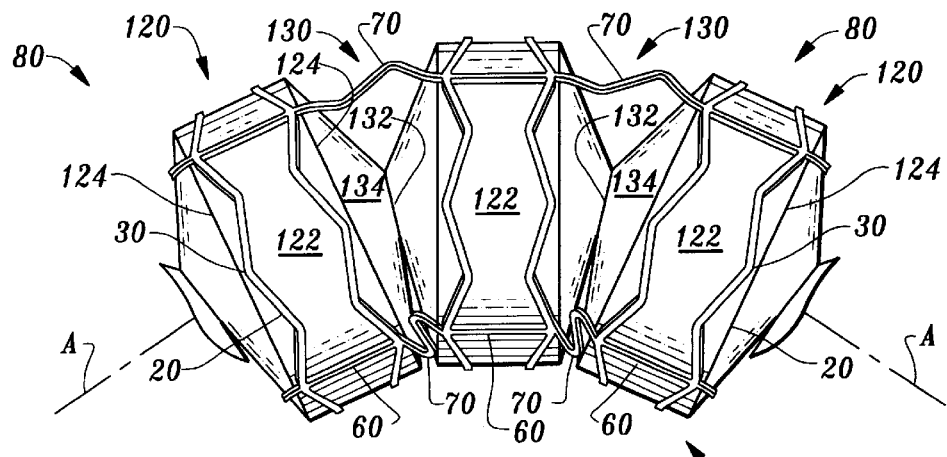
FIG. 8 is a front elevation view of a portion of that which is shown in FIG. 7 but with the stent and balloon flexed somewhat to cause a central axis of the balloon and stent to bend and showing an alternative embodiment of the segmented stent which includes flexible links joining adjacent segments of the segmented stent together.

The axial elements are preferably configured as tie bars 60 (FIGS. 3, 5 and 6), but can also be in other forms, such as flexible links 70 (FIG. 8). The tie bars 60 are substantially linear between a first junction 62 where the tie bar 60 attaches to one circumferential element 20 and a second junction 64 where the tie bar 60 attaches to another circumferential element 20 on an opposite side of the gap 40. Because the tie bars 60 are aligned axially, when axial forces are exerted on the tie bars 60 (in either a compression or tension fashion), such as when the stent 10 is trying to flex with the central axis A curving, the tie bars 60 resist such axial forces. This tendency of tie bars 60 to resist axial forces is beneficial when a stent 10 of greater strength, particularly in an axial direction, is desirable. This attribute of tie bars 60 allows the segments 80 to resist flexing and other distortion, so that flexibility of the stent 10 is concentrated at the unspanned gaps 45.

Figure 9:
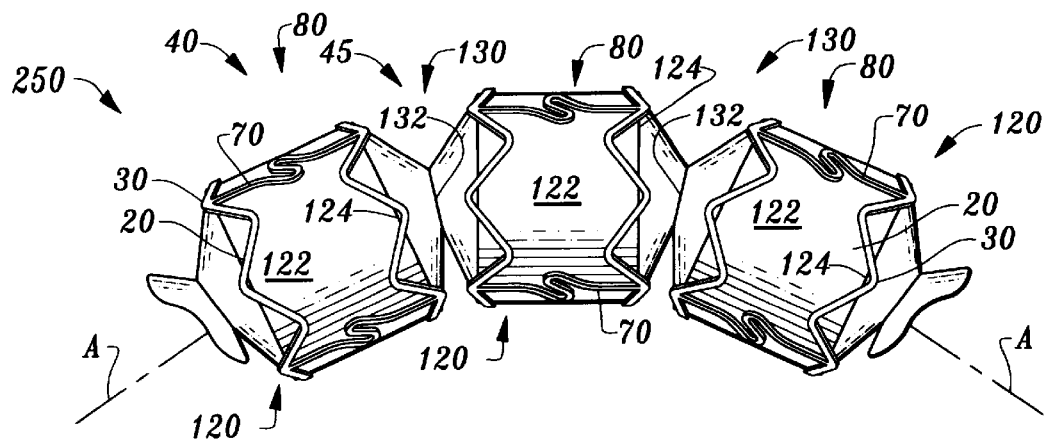
FIG. 9 is a front elevation view of that which is shown in FIG. 8 but with a slightly different flexible balloon configuration, with the circumferential elements of the segments of the stent only partially radially expanded and with flexible links joining the circumferential elements of each segment together.

Preferably, the tie bars 60 span each gap 40 between circumferential elements 20 in each segment 80 of the stent 10. Alternatively, at least some of the gaps 40 can be spanned by the flexible links 70 (FIG. 9). Most preferably, a set of three tie bars 60 span each gap 40 and the gaps between segments 80 remain unspanned gaps 45.

Preferably, each circumferential element 20 is out of phase with adjacent circumferential elements 20 so that the gaps 40 do not have a uniform width. Rather, the gaps 40 have a series of minimums 42 and maximums 44 (FIGS. 3, 5 and 6). The minimums 42 define portions of each gap 40 between crests 36 of adjacent circumferential elements 20. The maximums 44 define portions of each gap 40 adjacent troughs 32 of adjacent circumferential elements 20. Preferably, the tie bars 60 span the gaps 40 at maximums 44 in the gap 40. Alternatively, the tie bars 60 can span the gap 40 at minimums 42. If the circumferential elements 20 are in phase with each other, the tie bars 60 can extend between a trough 32 and a crest 36.

It will be noticed from a careful review of FIG. 6 that the circumferential elements 20 can be radially expanded to a point where the circumferential elements 20 are nearly circular in shape and have been radially expanded fully to a diameter of maximum radial expansion. Most prior art stents do not radially expand fully and hence cannot be radially expanded as much as the stent 10. While full radial expansion is not required to provide the stent 10 with all of the benefits disclosed herein, full radial expansion beneficially allows the surgeon to select a stent having a desired maximum radial expansion and then use a balloon 110 or other expansion device for exerting a radial force on the stent 10 which does not need to be perfectly matched to the amount of radial expansion desired.

Specifically, many prior art stents must be delivered with a balloon which can only expand a predefined amount radially and so the balloon and the stent 10 must be carefully matched together in configuration. With a fully expanded stent 10, as shown in FIG. 6, a balloon 110 which is capable of expanding the stent beyond the fully expanded diameter can be used and when the circumferential elements 20 are fully expanded, the stent 10 will restrain the balloon 110 from further expanding and the stent 10 will have been radially expanded the precise amount desired. This is particularly advantageous where the stent has circumferential elements 20 which have different diameters after radial expansion (FIG. 16) so that the stent 10 has a non-cylindrical contour, in that it allows a balloon 110 which is oversized (FIG. 17) to fully radially expand each of the circumferential elements 20 forming the stent 10. The surgeon need merely ensure that a pressure exerted by the balloon 110 does not exceed the ability of the circumferential elements 20 of the stent 10 to resist so that the circumferential elements 20 are not broken by forces exerted by the balloon 110 or other radial expansion device.

With particular reference to FIGS. 4–6, particular details of each segment 80 of the segmented stent 10 are described. Each segment 80 preferably includes two end circumferential elements 20 which have a spanned gap 40 there between. The spanned gap 40 includes linear tie bars 60 preferably coupling to troughs 32 in the adjacent circumferential elements 20. Because the tie bars 60 are linear, the tie bars 60 resist axial elongation or shortening. The tie bars 60 thus cause the segments 80 to resist flexing between the two end circumferential elements 20. Each tie bar 60 includes a first junction 62 attached to a trough of one of the end circumferential elements 20 and a second junction 64 attached to a trough in the other of the end circumferential elements 20. This location of the tie bars 60 causes the circumferential elements 20 to maintain a spacing there between when the segmented stent 10 is radially expanded and the segments 80 are correspondingly caused to radially expand.

Alternatively, the tie bars 60 can span minimums 42 in the gaps 40 and be shortened accordingly. When the tie bars 60 extend crest 36 to crest 36 the segment 80 is axially shortened when radially expanded. The shorter axial the entire segmented stent 10, the greater the number of segments 80 which can be provided for a given axial length of the stent 10. More segments 80 within a given length of the stent 10 translate into more flexibility overall and greater radial strength. The unspanned gaps 45 would typically be shortened axially in a stent 10 with such alternative segments 80. The gaps 45 would widen axially when the segments 80 adjacent the gap 45 axially shorten upon radial expansion. Of course, the stent 10 could also have a combination of segments 80 with trough 32 to trough 32 tie bars 60 and segments 80 with crest 36 to crest 36 tie bars 60.

The spanned gap 40 includes minimums 42 which are preferably as small as possible before radial expansion of the segments 80 of the segmented stent 10. In contrast, the unspanned gaps 45 (FIG. 3) are wider than the spanned gaps 40. The maximums 44 in the spanned gaps 40 preferably have an axial width similar to an axial length of the tie bars 60. After the segments 80 are radially expanded along with the segmented stent 10, the minimums 42 in the spanned gaps 40 increase in axial width approaching the axial width of the maximums 44 (FIG. 6).

Flexing of the segmented stent 10 occurs between the adjacent segments 80 in the unspanned gaps 45. An axial length of the unspanned gaps 45 is maintained by the flexible balloon 110 upon which the segmented stent 10 is initially mounted before delivery within the body lumen (FIG. 7).

With particular reference to FIGS. 7–10, basic details of the flexible balloon 110 and alternative embodiments for the configuration of the segmented stent 10 are described. The flexible balloon 110 is a hollow container having an interior spaced from an outer surface 122. The interior is in communication with a source of fluid under pressure which can be delivered to the interior to inflate and radially expand the balloon 110. The balloon 110 is formed to have a geometry including a distal end 112 spaced from a proximal end 114. The distal end 112 would typically support a guide wire to assist the surgeon in locating the flexible balloon and the segmented stent 10 mounted thereon to the appropriate implantation site. The proximal end 114 would typically support a fluid supply conduit leading to the interior and additionally support the guide wire controlled by the surgeon. The flexible balloon 110 includes a distal taper 116 adjacent the distal end 112 and a proximal taper 118 adjacent the proximal end 114. The tapers 116, 118 transition a radial size of the flexible balloon 110 from that at the ends 112, 114 to that at cylindrical sections 120 located between the distal end 112 and the proximal end 114.

The cylindrical sections 120 preferably have an outer surface 122 which is substantially cylindrical in form between two edges 124. The cylindrical sections 120 are spaced from adjacent cylindrical sections 120 by notches 130. Each notch 130 preferably includes a crease 132 defining a point of minimum radial size within each notch 130 and a conical surface 134 extending between each crease 132 and each edge 124 of the cylindrical sections 120 adjacent each notch 130.

The material forming the flexible balloon 110 is preferably substantially inelastic but flexible, such as a polyester or Teflon material. It is molded to the contour desired for the flexible balloon 110 and is formed with a substantially constant wall thickness and impervious to the passage of fluids therethrough under pressures up to twenty atmospheres.

The cylindrical sections 120 of the balloon 110 would typically have an outer surface 122 which is substantially cylindrical but which would tend to bulge somewhat at a midpoint between the edges 124 of each cylindrical section 120. The conical surfaces 134 within the notches 130 would be substantially conical but would bulge outward somewhat when the balloon 110 is inflated. Because the flexible balloon 110 is made from substantially inelastic material, the flexible balloon 110 is folded into its uninflated collapsed form before the segmented stent 10 is compressed around the outer surface 122 of the balloon 110. When the balloon 110 is inflated, the outer surface 122 unfolds and the balloon 110 assumes its inflated and radially expanded form with the cylindrical sections 120 substantially cylindrical in form (FIG. 6).

Figure 10:
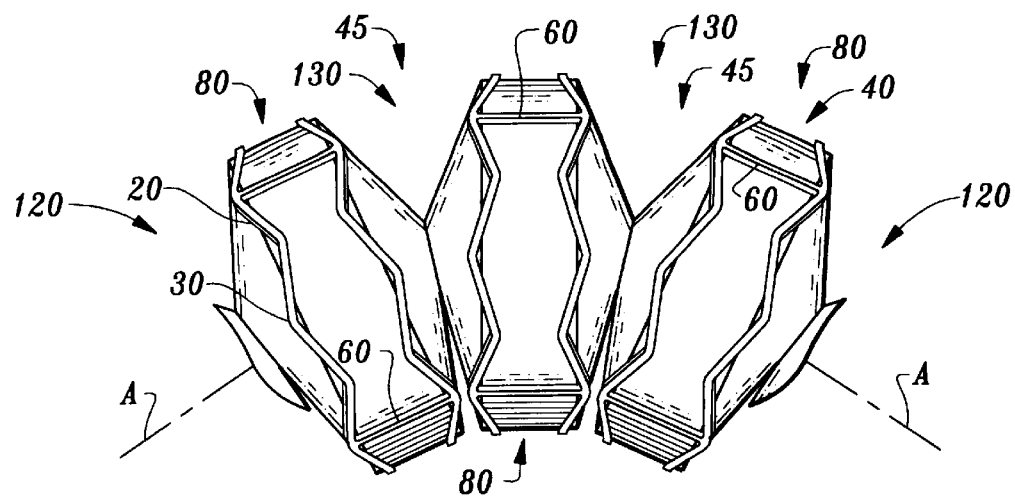
FIG. 10 is a front elevation view of a portion of that which is shown in FIG. 7 but with a central axis bent.

The segments 80 of the segmented stent 10 are located so that one segment 80 overlies the outer surface 122 of each cylindrical section 120. An axial width of each segment 80 between the end circumferential elements 20 is sized to substantially match an axial length of each cylindrical section 120 between the edges 124. Preferably, and as shown in FIGS. 7 and 10, the bends 30 in the end circumferential elements 20 slightly extend beyond the edges 124 of the cylindrical sections 120 and extend slightly out over the notches 130. Additionally, these bends 30 preferably are crimped down radially toward the central axis A slightly to additionally ensure that the segments 80 remain attached to the cylindrical section 120 of the balloon 110 during implantation of the balloon 110 when the balloon 110 and segmented stent 10 have not yet been radially expanded but are being passed through the body lumen on their way to the segmented stent 10 implantation site.

With particular reference to FIG. 8, a segmented stent 210 with each of the gaps spanned by an axial element is described. This alternative stent 210 is similar to the segmented stent 10 of the preferred embodiment except that the unspanned gaps 45 of the preferred embodiment (FIG. 7) are spanned by flexible links 70 in this alternative embodiment. The flexible links 70 join adjacent segments 80 together. The flexible links 70 can be extended or contracted in axial length so that the central axis A is allowed to bend and allowing the stent 210 to flex similar to the segmented stent 10 of the preferred embodiment. The flexible links 70 are located so that they span the notches 130 in the flexible balloon 110. Hence, regions of flexibility in the stent 210 are aligned with the regions of flexibility in the balloon 110. The segmented stent 210 includes segments 80 with end circumferential elements 20 joined together by linear tie bars 60 such that the segments 80 do not flex appreciably themselves but rather the stent 210 exhibits flexibility where the flexible links 70 join the segments 80 together.

With particular reference to FIG. 9, a stent 250 providing an alternative embodiment to the segmented stent 10 of the preferred embodiment (FIG. 7) is described. The alternative stent 250 includes segments 80 which are spaced from each other by unspanned gaps 45 similar to the segmented stent 10 of the preferred embodiment. However, the circumferential elements 20 of each segment 80 in the alternative stent 250 are joined together by flexible links 70 rather than linear tie bars 60 as in the segmented stent 10 of the preferred embodiment (FIG. 10). This alternative stent 250 primarily still provides flexibility at the unspanned gaps 45. Additionally, some flexibility is provided within each of the segments 80 by providing flexible links 70 spacing the two end circumferential elements 20 of each segment 80 from each other.

With particular reference to FIG. 10, a detail of a portion of the segmented stent 10 of the preferred embodiment is provided with the central axis A shown bent and illustrating how the segments 80 remain unflexed themselves but the unspanned gaps 45 between adjacent segments 80 are flexed to allow the segmented stent 10 to flex. While the segments 80 of the segmented stent 10 preferably are provided with two circumferential elements 20 out of phase with each other and joined together by linear tie bars 60, various different configurations for the segments 80 could similarly be provided. For instance, the segments 80 could be provided with more than two circumferential elements 20 spaced axially from each other and the circumferential elements 20 could be in arrangements other than out of phase with each other. Also, the axial width of the segments 80 can be adjusted so that the end circumferential elements 20 remain entirely supported by the cylindrical sections 120 and inboard of the edges 124 on the flexible balloon 110, rather than overlapping the edges 124 somewhat and extending over the notches 130.

In use and operation and with particular reference to FIGS. 11–13, details of the utilization of the overall flexible stent delivery system having the segmented stent 10 therein is described. Initially, the segmented stent 10 has a number of segments 80 selected which preferably matches (or is less than) the number of cylindrical sections 120 on the flexible balloon 110. The non-inflated collapsed balloon 110 has the segments 80 collapsed down onto the cylindrical sections 120 so that the balloon 110 and segmented stent 10 have a minimum diameter (FIG. 11). A surgeon can then pass the balloon 110 and stent 10 stent delivery system, mounted upon an appropriate guide wire and with an appropriate fluid inflation conduit, through the intended body lumen until the stent 10 and balloon 110 are positioned where desired. As the segmented stent 10 and balloon 110 pass through tight bends in the body lumen, the notches 130 and unspanned gaps 45 allow the balloon 110 and segmented stent 10 to flex sufficiently to navigate through these tight bends in the body lumen (FIG. 11).

Once the segmented stent 10 and balloon 110 are positioned where desired, the fluid is passed into the interior of the balloon 110 under sufficient pressure to inflate the balloon 110 and radially expand the individual segments 80 of the segmented stent 10 (FIG. 12). When the balloon 110 is inflated and expanded, the notches 130 and the balloon 110 allow the balloon 110 to resist resulting straightening forces exerted on the balloon 110. Hence, the balloon 110 and segmented stent 10 can maintain their flexed configuration during the inflation and radial expansion process. Once the segments 80 of the segmented stent 10 have been inflated as desired, the fluid pressure is released so that the outer surface 122 of the balloon 110 is no longer exerting a radial force on the segmented stent 10. The balloon 110 can then be removed axially along with the guide wire so that the segmented stent 10 is left alone within the body lumen L (FIG. 13).

With particular reference to FIGS. 14–17, details of a segmented stent 310 with varying diameter segments is described. The varying diameter segmented stent 310 is similar to the segmented stent 10 of the preferred embodiment except that the varying diameter segmented stent 310 includes both segments 80 and small segments 90. The small segments 90 differ from the segments 80 in that the small segments 90 have a diameter of maximum radial expansion which is less than that of the segments 80. Hence, the segments 80 are larger in diameter than the small segments 90.

Preferably, the small segments 90 are configured so that both the segments 80 and small segments 90 have a common radial diameter when the segments 80, 90 are collapsed onto the cylindrical sections 120 of the balloon 110 (FIG. 15). When the balloon 110 and varying diameter segmented stent 310 are positioned where desired, the balloon 110 is inflated (FIG. 16). The segments 80 are expanded to their maximum diameter of radial expansion and the small segments 90 are expanded to their maximum diameter of radial expansion. Hence, the varying diameter segmented stent 310 is left with some portions of the varying diameter segmented stent 310 having a larger diameter than other portions.

The small segments 90 restrain the cylindrical sections 120 of the balloon 110 that are adjacent to the small segments 90 from being fully radially expanded when the balloon 110 is inflated. FIG. 17 depicts how the balloon 110 would appear if no varying diameter segmented stent 310 were located thereon. The small segments 90 are provided with sufficient strength so that they can resist the radial forces away from the central axis A and along arrow R (FIG. 1) when the small segments 90 are being inflated. Thus, the cylindrical sections 120 adjacent the small segments 90 do not burst the small segments 90, but rather the small segments 90 merely restrain the cylindrical sections 120 adjacent the small segments 90 from being fully radially expanded. Alternatively, the balloon 110 can be configured so that it tapers in a manner conforming with the sizes of the stent segments 80, 90 located adjacent the various cylindrical sections 120 of the balloon 110.

This disclosure is provided to reveal a preferred embodiment of the invention and a best mode for practicing the invention. Having thus described the invention in this way, it should be apparent that various different modifications can be made to the preferred embodiment without departing from the scope and fair meaning of this disclosure.

What is claimed is:

1. A flexible radially expandable stent for implantation into a body lumen, the stent comprising in combination:

at least three circumferential elements, each said circumferential element having a wave-like series of bends therein as each said circumferential element circumscribes a central axis of said stent, each said bend including a trough and a crest, said trough defining a portion of said circumferential element where said circumferential element is more distant from adjacent said circumferential elements than other portions of said circumferential element, said crest defining a portion of said circumferential element where said circumferential element is closer to adjacent circumferential elements than other portions of said circumferential element;

at least two gaps, each of said at least two gaps located between a different adjacent pair of said at least three circumferential elements;

at least one of said gaps being a spanned gap spanned by an axial element, said axial element having ends attached to said circumferential elements adjacent said spanned gap;

at least one of said gaps being an unspanned gap, such that said circumferential elements adjacent said unspanned gap are not connected together;

wherein an axial width of said unspanned gap remains substantially constant during and after implantation of said stent;

wherein said spanned gaps are axially narrower than said unspanned gaps before radial expansion of said stent;

wherein a pair of said circumferential elements located adjacent said spanned gap form one segment, said stent including at least two segments, said stent including an unspanned gap between said at least two segments; and wherein said spanned gaps alternate with said unspanned gaps between pairs of adjacent said circumferential elements throughout said stent.

2. The stent of claim 1 wherein said spanned gaps are spanned by substantially inflexible axial elements, such that flexing of said stent occurs at said unspanned gaps rather than at said spanned gaps.

3. The stent of claim 2 wherein said axial elements of said spanned gaps attach to said circumferential elements adjacent said spanned gaps at troughs in said bends of said adjacent circumferential elements, such that no axial contraction of said segments occurs when said stent is radially expanded.

4. A stent delivery system for implantation within a body lumen of non-uniform diameter, the system comprising in combination:

a stent having at least two segments, each said segment including at least two circumferential elements located axially spaced from each other at axial ends of said segment;

each of said at least two circumferential elements having a wave-like series of bends therein as each said circumferential element circumscribes a central axis of said stent, each said bend including a trough and a crest, said trough defining a portion of said circumferential element where said circumferential element is more distant from adjacent said circumferential elements than other portions of said circumferential element, said crest defining a portion of said circumferential element where said circumferential element is closer to adjacent circumferential elements than other portions of said circumferential element;

said segments having different diameters of maximum radial expansion;

an inflatable balloon having an interior surrounded by an outer surface, said outer surface extending radially from a central axis when said balloon is inflated, said balloon having an inflated diameter at least as great as a diameter of maximum radial expansion of a larger of said segments adjacent said larger segment and an inflated diameter at least as great as a diameter of maximum radial expansion of a smaller of said segments adjacent said smaller segment; and wherein said outer surface of said balloon has a substantially constant inflated radial size at locations on said outer surface of said balloon adjacent said at least two stent segments.

5. The system of claim 4 wherein said smaller segment of said stent is radially stronger than radial expansion forces of said balloon when said balloon is expanded, so that said balloon is restricted from full expansion adjacent said smaller segment of said stent when said balloon is inflated.

6. The system of claim 5 wherein said balloon includes at least two separate sections axially spaced from each other;

wherein said outer surface has at least one notch between said at least two sections, said notch defining a portion of said balloon having a radial size less than a radial size of said outer surface at said at least two sections when said balloon is inflated; and wherein said segments of said stent line up with said sections of said outer surface of said balloon.

7. The system of claim 6 wherein said stent includes at least one gap between said at least two segments, said gap spanned by an axial element having greater flexibility than a flexibility of axial elements spanning gaps between said at least two circumferential elements of each said segment.

8. The system of claim 6 wherein said stent includes at least one gap between said at least two segments, said at least one gap being an unspanned gap, such that said circumferential elements adjacent said unspanned gap are not connected together.

9. The system of claim 8 wherein each of said sections terminates axially at edges, said circumferential elements at said axial ends of at least one said stent segment adjacent one of said sections remaining at least partially inboard of said edges of said section.

10. The system of claim 9 wherein said at least two circumferential elements at said axial ends of said at least one stent segment each extend partially beyond said edges of said section adjacent said segment in which said at least two circumferential elements are located; and wherein said circumferential elements each extend radially inward toward said central axis on portions of said circumferential elements which extend beyond said edges and over said notches in said balloon.

11. A flexible stent delivery system comprising in combination:

an inflatable balloon having an interior surrounded by an outer surface, said outer surface extending radially from a central axis when said balloon is inflated;

said outer surface having at least two separate sections axially spaced from each other;

said outer surface having at least one notch between said at least two sections, said notch defining a portion of said balloon having a radial size less than a radial size of said outer surface at said at least two sections when said balloon is inflated; and a radially expandable stent having a first collapsed radial size matching a radial size of said outer surface at said sections before said balloon is inflated and a second expanded radial size matching a radial size of said outer surface of said sections after said balloon is inflated.

12. The system of claim 11 wherein said stent includes at least two separate segments, each said segment having two end circumferential elements at ends of each said segment, said end circumferential elements of each said segment sufficiently close together to be at least partially overlying a common one of said at least two sections in said outer surface of said balloon; and wherein said end circumferential elements of each of said at least two segments are coupled together by at least one axial element spanning a gap between said end circumferential elements.

13. The system of claim 12 wherein said stent exhibits greater axial flex where said stent overlies said at least one notch in said outer surface of said balloon than an axial flexibility exhibited by said stent adjacent said at least two sections in said outer surface of said balloon.

14. The system of claim 13 wherein said at least one axial element joining said end circumferential elements is free of bends and gaps between adjacent said at least two stent segments and overlying said at least one notch in said outer surface of said balloon is spanned by an axial element including at least one bend therein, such that said bend allows said axial element spanning said gap between said stent segments to exhibit some axial adjustment in length to facilitate axial flexing of said at least two stent segments relative to each other.

15. The system of claim 13 wherein gaps between said at least two stent segments and overlying said at least one notch in said outer surface of said balloon are unspanned, such that said end circumferential elements adjacent said unspanned gap are not connected together.

* * * * *